(12) United States Patent
Siddiqui et al.

(10) Patent No.: US 12,216,620 B2
(45) Date of Patent: Feb. 4, 2025

(54) SYSTEM AND METHODS FOR MASSIVE DATA MANAGEMENT AND TAGGING

(71) Applicant: Intellix.AI Inc., Culpepper, VA (US)

(72) Inventors: Khan Mohammad Siddiqui, Hinsdale, IL (US); Robert Bakos, Carol Stream, IL (US); Gerard M. Stegmaier, Culpepper, VA (US); Oliver Szu-Ping Chen, Woodside, CA (US); Jack Cosgrove, Culpepper, VA (US)

(73) Assignee: Intellix.AI Inc., Culpepper, VA (US)

( * ) Notice: Subject to any disclaimer, the term of this patent is extended or adjusted under 35 U.S.C. 154(b) by 0 days.

(21) Appl. No.: 17/680,191

(22) Filed: Feb. 24, 2022

(65) Prior Publication Data

US 2022/0276985 A1  Sep. 1, 2022

Related U.S. Application Data

(60) Provisional application No. 63/154,436, filed on Feb. 26, 2021.

(51) Int. Cl.
*G06F 16/16* (2019.01)
*G16H 30/40* (2018.01)

(52) U.S. Cl.
CPC .......... *G06F 16/166* (2019.01); *G06F 16/162* (2019.01); *G06F 16/168* (2019.01); *G16H 30/40* (2018.01)

(58) Field of Classification Search
CPC .... G06F 16/166; G06F 16/162; G06F 16/168; G16H 30/40; G16H 30/20; G16H 50/70
See application file for complete search history.

(56) References Cited

U.S. PATENT DOCUMENTS

| | | | |
|---|---|---|---|
| 2013/0346455 A1* | 12/2013 | Prasad | G06F 16/972 707/825 |
| 2014/0010421 A1* | 1/2014 | Colaco | G16H 30/40 382/128 |
| 2016/0004820 A1* | 1/2016 | Moore | G16H 15/00 705/3 |
| 2016/0027051 A1* | 1/2016 | Gross | G06V 20/20 705/14.54 |
| 2016/0048934 A1* | 2/2016 | Gross | G06V 10/40 705/313 |
| 2016/0092959 A1* | 3/2016 | Gross | G06Q 30/0625 705/26.62 |
| 2016/0217195 A1* | 7/2016 | Abrahams | H04L 67/306 |
| 2017/0213127 A1* | 7/2017 | Duncan | G16B 50/30 |

(Continued)

*Primary Examiner* — Angelica Ruiz
(74) *Attorney, Agent, or Firm* — Kilpatrick Townsend & Stockton LLP (57) ABSTRACT

System and methods for massive data management and tagging are disclosed herein. A method for automated file linking can include creating a sample set of files from a set of files, at least some of the files including metadata. The method can include identifying common metadata between files in the sample set of files from the file set, and identifying at least one link, one of which links can include the common metadata between files in the sample set of files. The method can include identifying files in the set of files, each of the identified files containing the link in their metadata, generating an association between the files containing the link in their metadata, and storing the association between the files containing the link in their metadata.

22 Claims, 5 Drawing Sheets

(56) References Cited

U.S. PATENT DOCUMENTS

2019/0026322 A1\* 1/2019 Gerweck ................ G06Q 30/02
2019/0034083 A1\* 1/2019 Cherubini ............. G06F 3/0685
2019/0208014 A1\* 7/2019 Goldberg ............ G06F 21/6218
2021/0133148 A1\* 5/2021 Gotkhindikar .......... G06F 16/13
2022/0076804 A1\* 3/2022 Palmer ................... G16H 50/70

\* cited by examiner

SYSTEM AND METHODS FOR MASSIVE DATA MANAGEMENT AND TAGGING

CROSS-REFERENCE TO RELATED APPLICATIONS

This application claims priority to Provisional U.S. Patent Application No. 63/154,436 filed Feb. 26, 2021, entitled "SYSTEM AND METHODS FOR MASSIVE DATA MANAGEMENT AND TAGGING," the entire disclosure of which is hereby incorporated by reference, for all purposes, as if fully set forth herein.

BACKGROUND

Techniques described herein relate to network security, data security, and data management and storage. The evolution of big data analytics and machine learning techniques has been excited and led to the advance of many fields of technology. Leveraging big data and machine learning frequently uses large volumes of data from heterogeneous sources or of great variety in scope to ensure robustness of any given technique or model. Collaboration between generators of content data may enable the wide-scale aggregation of content data and may thereby help ensure robustness of techniques or models.

However, such collaboration to allow the aggregation of a large and robust data set is not simple. Indeed, many issues relating to the collaboration can arise. These can include issues relating to the storing of the volume of data that may aggregated via the collaboration, curating this data, and maintaining adequate protection of the data to entice further collaboration. While there have been developments to address aspects of these concerns, complete solutions to such problems have not been found. Accordingly, further technological innovation is desired to address these current shortcomings.

BRIEF SUMMARY

One aspect of the present disclosure relates to a system for automated file linking. The system can include at least one database server including stored data including a set of files. In some embodiments, at least some of the files include metadata. The system can include at least one server. The at least one server can create a sample set of files from the set of files, identify common metadata between files in the sample set of files, identify at least one link, which link includes the common metadata between files in the sample set of files, identify files in the set of files, each of the identified files containing the link in their metadata, generate an association between the files containing the link in their metadata, and store the association between the files containing the link in their metadata.

In some embodiments, the at least one database server can receive the set of files. In some embodiments, the at least one server can create the sample set of files from the set of files. In some embodiments, the at least one server can: extract metadata from files in the sample set of files, and compare metadata extracted from the files in the sample set of files. In some embodiments, common metadata between files in the sample set of files is identified based on the comparing of metadata extracted from the files in the sample set of files.

In some embodiments, the at least one server can generate a list of potential links, which list of potential links identifies common metadata, present the list of potential links to a user, and receive a user input. In some embodiments, the at least one link is from the list of potential links and is identified based on the received user input. In some embodiments, the at least one server can link all metadata of files containing the link in their metadata.

In some embodiments, the at least one server can delete extraneous metadata from associated files. In some embodiments, the extraneous metadata includes metadata not in an identified link. In some embodiments, the at least one server can create a set of identified links, and standardize naming of the identified links. In some embodiments, the at least one server can identify similar links among the identified links. In some embodiments, standardizing naming of the identified links includes consolidating similar links under a single link. In some embodiments, the at least one server can store standardizingly named identified links.

One aspect of the present disclosure relates to a method of automated file linking. The method includes creating a sample set of files from a set of files, at least some of the files including metadata, identifying common metadata between files in the sample set of files from the file set, identifying at least one link, identifying files in the set of files, each of the identified files containing the link in their metadata, generating an association between the files containing the link in their metadata, and storing the association between the files containing the link in their metadata. In some embodiments, a link can include the common metadata between files in the sample set of files.

In some embodiments, the method includes receiving a set of files. In some embodiments, the method includes creating a sample set of files from the set of files. In some embodiments, the method includes extracting metadata from files in the sample set of files, and comparing metadata extracted from the files in the sample set of files. In some embodiments, common metadata between files in the sample set of files is identified based on the comparing of metadata extracted from the files in the sample set of files.

In some embodiments, the method includes generating a list of potential links, which list of potential links identifies common metadata, presenting the list of potential links to a user, and receiving a user input. In some embodiments, the at least one link is from the list of potential links and is identified based on the received user input. In some embodiments, the method includes linking all metadata of files containing the link in their metadata.

In some embodiments, the method includes deleting extraneous metadata from associated files. In some embodiments, extraneous metadata includes metadata not in an identified link. In some embodiments, the method includes creating a set of identified links, and standardizing naming of the identified links. In some embodiments, the method includes identifying similar links among the identified links. In some embodiments, standardizing naming of the identified links includes consolidating similar links under a single link. In some embodiments, the method includes storing standardizingly named identified links.

One aspect of the present disclosure relates to a system for transforming and compressing tags. The system includes at least one database server including stored data including a set of files, at least some of the files including metadata. The system can include at least one server. The at least one server can select a tag associated with a file, determine a tag attribute, generate a single string representing the tag, select one of a plurality of fields of a field portion of a document of the file, and store the single string in the selected one of the plurality of fields. In some embodiments, the one of the plurality of fields is selected based on the determined tag attribute.

In some embodiments, the tags can be DICOM tags. In some embodiments, the at least one server can select a file, and identify at least one tag associated with the selected file. In some embodiments, the tag is selected from the at least one tag associated with the selected file. In some embodiments, the tag can include a key-value pair.

In some embodiments, determining the tag attribute includes determining that the key-value pair includes a string. In some embodiments, generating a single string representing the tag includes identifying a key and the tag value of the tag, and combining the key of the tag value of the tag into a single string. In some embodiments, the one of the plurality of fields of the field portion of the document of the file corresponds to tags including a string. In some embodiments, the key of the tag includes a group and an element. In some embodiments, each of the group and the element includes a 2-byte number. In some embodiments, the tag value includes a string represented by at least a 2-byte integer number.

In some embodiments, determining the tag attribute includes determining that the key-value pair includes a number. In some embodiments, the at least one server can determine that the number is at least one of a signed number, an unsigned number, and a floating point number. In some embodiments, the plurality of fields includes a first field for signed numbers, a second field for unsigned numbers, and a third field for floating point numbers. In some embodiments, determining the tag attribute further includes determining a size of the tag. In some embodiments, determining the size of the tag includes determining the size of number of the tag value of the key-value pair.

In some embodiments, the method includes comparing the size of the tag to a threshold range, and determining that the size of the tag is within the threshold range. In some embodiments, generating a single string representing the tag includes identifying a key of the tag, and combining the key and the tag value of the tag into a single string. In some embodiments, the threshold range includes a first threshold range when the number is a signed number, and in some embodiments, the threshold range includes a second threshold range when the number is an unsigned number. In some embodiments, storing the single string in the selected one of the plurality of fields includes storing the single string in the first field when the number is a signed number, storing the single string in the second field when the number is an unsigned number, and storing the single string in the third field when the number is a floating point number.

In some embodiments, the at least one server can compare the size of the tag to a threshold range, determine that the size of the tag is outside the threshold range, determine that the tag is a long-type tag, and convert the tag value of the tag to a string representation. In some embodiments, generating a single string representing the tag includes identifying a key, and combining the key and the string representation of the tag value of the tag into a single string. In some embodiments, the string representation comprises a hexadecimal number.

One aspect of the present disclosure relates to a method for transforming and compressing tags. The method includes selecting a tag associated with a file, determining a tag attribute, generating a single string representing the tag, selecting one of a plurality of fields of a field portion of a document of the file, which one of the plurality of fields is selected based on the determined tag attribute, and storing the single string in the selected one of the plurality of fields.

In some embodiments, the tags can be DICOM tags. In some embodiments, the method includes selecting a file, and identifying at least one tag associated with the selected file. In some embodiments, the tag is selected from the at least one tag associated with the selected file. In some embodiments, the tag can be a key-value pair.

In some embodiments, determining the tag attribute includes determining that the key-value pair includes a string. In some embodiments, generating a single string representing the tag includes identifying a key and the tag value of the tag, and combining the key of the tag value of the tag into a single string. In some embodiments, the one of the plurality of fields of the field portion of the document of the file corresponds to tags including a string. In some embodiments, the key of the tag includes a group and an element. In some embodiments, each of the group and the element can be a 2-byte number. In some embodiments, the tag value can be a string represented by at least a 2-byte integer number.

In some embodiments, determining the tag attribute includes determining that the key-value pair includes a number. In some embodiments, the method includes determining that the number is at least one of: a signed number, an unsigned number, and a floating point number. In some embodiments, the plurality of fields includes a first field for signed numbers, a second field for unsigned numbers, and a third field for floating point numbers. In some embodiments, determining the tag attribute further includes determining a size of the tag. In some embodiments, determining the size of the tag includes determining the size of number of the tag value of the key-value pair.

In some embodiments, the method includes comparing the size of the tag to a threshold range, and determining that the size of the tag is within the threshold range. In some embodiments, generating a single string representing the tag includes identifying a key of the tag, and combining the key and the tag value of the tag into a single string. In some embodiments, the threshold range includes a first threshold range when the number is a signed number. In some embodiments, the threshold range includes a second threshold range when the number is an unsigned number. In some embodiments, storing the single string in the selected one of the plurality of fields includes storing the single string in the first field when the number is a signed number, storing the single string in the second field when the number is an unsigned number, and storing the single string in the third field when the number is a floating point number.

In some embodiments, the method includes comparing the size of the tag to a threshold range, determining that the size of the tag is outside the threshold range, determining that the tag is a long-type tag, and converting the tag value of the tag to a string representation. In some embodiments, generating a single string representing the tag includes identifying a key, and combining the key and the string representation of the tag value of the tag into a single string. In some embodiments, the string representation includes a hexadecimal number.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

The present disclosure is described in conjunction with the appended figures.

In the figures, similar backings and/or features may have the same reference label. Where the reference label is used in the specification, the description is applicable to any one of the similar backings having the same reference label.

DETAILED DESCRIPTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It is understood that various changes may be made in the function and arrangement of elements without departing from the spirit and scope as set forth in the appended claims.

The rise of big data has led to the simultaneous rise of big data-based problems. These include storing large volumes of data and making these large volumes of data searchable. Problems surrounding big data become particularly acute with certain types of files and/or file format. For example, with some file types, metadata is stored separately from the data forming the file, and specifically, each tag associated with the data forming the file can be stored in a separate file. The result of this is that each file may actually be the aggregate of a single file of data and tens or even hundreds of files of metadata. This large number of metadata files rapidly inflates the storage load of a data set.

This rapid inflation of storage load of a data set within a search index such as Elasticsearch can arise when the data set includes DICOM files (files following the Digital Imaging and Communications in Medicine standard). Each tag of a DICOM file must be stored as a separate nested document within the search index to maintain the searchability of that tag by its associated key, composed of DICOM standard fields called the group and element. Thus, each DICOM file may actually include at least one data document, and tens or hundreds of associated metadata documents for each tag. Due to this proliferation of metadata documents, inclusion of DICOM files in a search index can present significant problems. These problems can include slowing the search process.

In addition to this, large data sets are difficult to search. This difficulty arises from the fact that the files forming these large data sets are largely separate and distinct, and may come from a number of different sources. These difficulties in searching large data sets prevents the attainment of the maximum benefit from these data sets as it may be difficult, or in effect impossible, to find all of the desired pieces of data from such a data set.

Embodiments of the present disclosure relate to systems and methods for addressing these current limitations. Specifically, one embodiment of the present disclosure relates to systems and methods for transforming and/or compressing tags into a format to facilitate searchability of the data set.

This transformation and/or compressing of the tags can be intended to facilitate searchability of the data set via, for example, Elasticsearch.

In some embodiments, Elasticsearch can enable searching of a string, which can be a character string or a number represented by a bit string, and which string can have a length of up to 64 bits. Specifically, in some embodiments, the largest integer data type that can be represented by Elasticsearch can be a signed long having a 64 bit lengths. In some embodiments, representation of the DICOM tag key, including both the group and element, can use 32 bits, thus leaving 32 bits to represent the tag value.

32 bits for representing the numerical tag value is acceptable under most circumstances as most tag values can be represented by 32 bits or less. However, DICOM files support signed and unsigned data types. Because a signed value utilizes one bit to represent the sign, the range of tag values possible in a DICOM file changes dependent on whether the tag value is singed or unsigned. Due to this difference in covered range, signed and unsigned values cannot be represented in the same field. Further, each of signed and unsigned values have different maximum values that can be represented and be searchable via Elasticsearch.

This transforming and/or compressing of a tag can include converting a tag, which can be a key-value pair, into a single string, which single string can be, in some embodiments, a character string or a bit string representing a number, which number can be a single number. This single string can be created by identifying the different components of the key-value pair, and combining them together. These parts of the key-value pair can include the DICOM tag key, which can include a group and an element, which can be represented as the concatenation of the hexadecimal string representation of the group and element, and the tag value, separated from the key by a space. This tag value can be a string which can be, for example, a character string, or bit string representing a number.

In combining the key-value pair, a tag is identified and selected or retrieved. The key-value pair is extracted, and a characteristic of the key-value pair is determined. This characteristic can include, for example, whether the tag value is a character string, or a bit string representing a number. This characteristic can further include, if the tag value is a number, whether the number is signed, unsigned, or a floating point number.

If the tag value of the key-value pair is a character string, then the key and the tag value are combined into a single character string. If the tag value is a signed number having a value within a predetermined range for signed numbers, then the key, including the group and element can be combined with the tag value into a single number that can be stored in a field for signed numbers. If the tag value is an unsigned number having a value within a predetermined range for unsigned numbers, then the key, including the group and element, can be combined with the tag value into a single number that can be stored in a field for unsigned numbers. If the tag value is a floating point number having a value within a predetermined range for floating point values, then the key, including the group and element, can be combined with the tag value into a single number that can be stored in a filed for floating point numbers.

If, any of these numbers fall outside of their acceptable range, then the key-value pair can be identified as an overflow key-value pair. The key-value pair, and specifically the tag value of the key-value pair can be evaluated to determine if the tag value is a long type. If the tag value is a long type, and particularly is it is a long type unsigned number, then the tag value can be converted into a string representing the tag value, and in some embodiments, can be converted into a hexadecimal number represented as a character string. This representative string can then be combined with the key and stored. In some embodiments, this can be stored in a nested field, which can, in some embodiments, comprise an Elasticsearch nested field, which can result in the creation of a separate document containing the string representing the key-value pair including the string or number representing the tag value. If the overflow value is not a long type, then the key and the tag value can be stored in a nested field, which can, in some embodiments, comprise an Elasticsearch nested field, which can result in the creation of a separate, associated search index document containing the key-value pair.

Via application of this method, the number of metadata documents can be significantly reduced, in some embodiments only requiring nested documents for the overflow tags, thereby decreasing the storage load of a big data collection. Further, the merging of the key-value pair of tags into a single string and/or number can improve the searchability of the tags. Specifically, due to the decreasing in the number of documents for the tags, by representing some or all of the tags in fields of a single document, the search speed is significantly increased. This combination of key-value pairs into a single string still supports range queries applied only to the key.

Some embodiments of the present disclosure relate to improving searchability of files in a data set via the creation of a text-based search index. This can be performed based on an analysis of metadata associated with files in the data set. Specifically, a subset of the files in a data set can be identified and analyzed to identify one or several common metadata types. One or several of these common metadata types can be identified as a link. This identification can include presenting the common metadata types to a user and receiving a user input identifying at least one of the one or several common metadata types as a link.

The files in the data can be analyzed, and specifically the metadata of files in the dataset can be analyzed to identify files having metadata corresponding to the links. Specifically, the files in the data set can be analyzed to identify each file containing metadata corresponding to each of the identified links. Files containing metadata corresponding to a common one of the links can be associated. This can be repeated to thereby create associations between some or all of the files in the data set based on the inclusions of links in those files' metadata.

These associations can be stored. In some embodiments, extraneous metadata, which can include metadata not corresponding to a link, can be removed from files, and in some embodiments, all metadata of associated files can be associated. The links can be stored and associated files can be stored in association with their link. This can result in the creation of a database of links and files associated by each of the stored links. In some embodiments, this database can be searched to identify one or several groups of similar, and specifically of similarly named links. The naming of these similar links can be standardized such that, for example, a common name represents all of these similar links. This standardized name for a group of links can be stored.

In some embodiments, the generation of such a database can significantly improve the usability of a data set. This can include increasing the speed with which a search of the data set can be performed, and/or improving the accuracy of searches performed on the data set.

Figure 1:
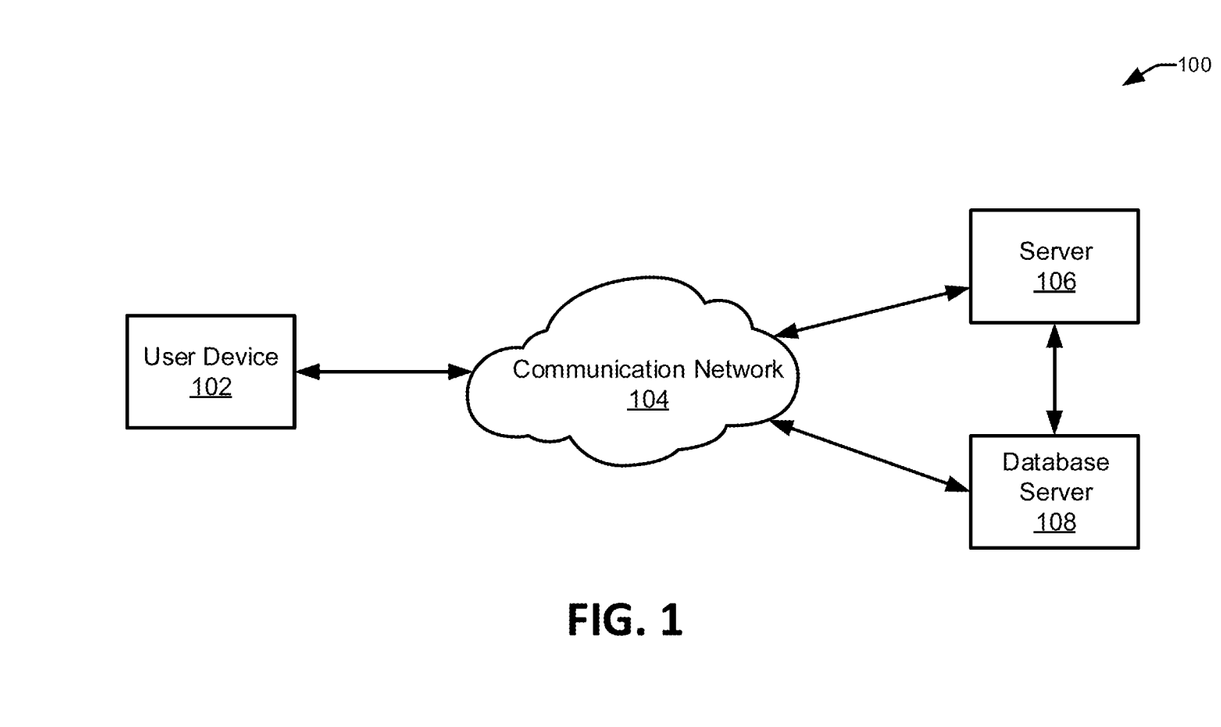
FIG. 1 is a schematic illustration of one embodiment of a network.

With reference now to FIG. 1, a schematic illustration of one embodiment of a network 100 is shown. The network 100 can be configured for use in gathering and/or aggregating data. In some embodiments, for example, data can be gathered from and/or received from a plurality of user devices 102 by a server 106 and/or a database server 108. The user device 102 can comprise any computing device and/or compute instance. This can include, for example, a smartphone, a tablet, a laptop computer, a personal computer, a server, a virtual machine, or the like.

The user device 102 can be communicatingly connected with the server 106 and/or the database server 108. In some embodiments, the user device 102 can be wired and/or wirelessly connected with the server 106 and/or the database server 108 via the communication network 104. In some embodiments, this communicating connection can be via the communication network 104 which can comprise, for example, a Local Area Network and/or a Wide Area Network. In some embodiments, the communication connection 104 can comprise the internet.

The server 106 can comprise one or several compute instances, some or all of which can comprise a physical server or a virtual machine running on one or several host machines. The server 106 can be configured to perform one or several operation in response to information and/or requests received from the user device 102.

The server 106 may be any desired type of server including, for example, a rack server, a tower server, a miniature server, a blade server, a mini rack server, a mobile server, an ultra-dense server, a super server, or the like, and may include various hardware components, for example, a motherboard, a processing unit, memory systems, hard drives, network interfaces, power supplies, etc. Server 106 may include one or more server farms, clusters, or any other appropriate arrangement and/or combination or computer servers. Server 106 may act according to stored instructions located in a memory subsystem of the server 106, and may run an operating system, including any commercially available server operating system and/or any other operating systems discussed herein.

The database server 108 can access data that can be stored on a variety of hardware components. These hardware components can include, for example, components forming tier 0 storage, components forming tier 1 storage, components forming tier 2 storage, and/or any other tier of storage. In some embodiments, tier 0 storage refers to storage that is the fastest tier of storage in the database server 108, and particularly, the tier 0 storage is the fastest storage that is not RAM or cache memory. In some embodiments, the tier 0 memory can be embodied in solid state memory such as, for example, a solid-state drive (SSD) and/or flash memory.

In some embodiments, the tier 1 storage refers to storage that is one or several higher performing systems in the memory management system, and that is relatively slower than tier 0 memory, and relatively faster than other tiers of memory. The tier 1 memory can be one or several hard disks that can be, for example, high-performance hard disks. These hard disks can be one or both of physically or communicatively connected such as, for example, by one or several fiber channels. In some embodiments, the one or several disks can be arranged into a disk storage system, and specifically can be arranged into an enterprise class disk storage system. The disk storage system can include any desired level of redundancy to protect data stored therein, and in one embodiment, the disk storage system can be made with grid architecture that creates parallelism for uniform allocation of system resources and balanced data distribution.

In some embodiments, the tier 2 storage refers to storage that includes one or several relatively lower performing systems in the memory management system, as compared to the tier 1 and tier 2 storages. Thus, tier 2 memory is relatively slower than tier 1 and tier 0 memories. Tier 2 memory can include one or several SATA-drives (e.g., Serial AT Attachment drives) or one or several NL-SATA drives.

In some embodiments, the one or several hardware and/or software components of the database server 108 can be arranged into one or several storage area networks (SAN), which one or several storage area networks can be one or several dedicated networks that provide access to data storage, and particularly that provides access to consolidated, block level data storage. A SAN typically has its own network of storage devices that are generally not accessible through the local area network (LAN) by other devices. The SAN allows access to these devices in a manner such that these devices appear to be locally attached to the user device.

Data stores 108 may comprise stored data relevant to the functions of the content network 100. In some embodiments, multiple data stores may reside on a single server 108, either using the same storage components of server 108 or using different physical storage components to assure data security and integrity between data stores. In other embodiments, each data store may have a separate dedicated data store server 108.

Figure 2:
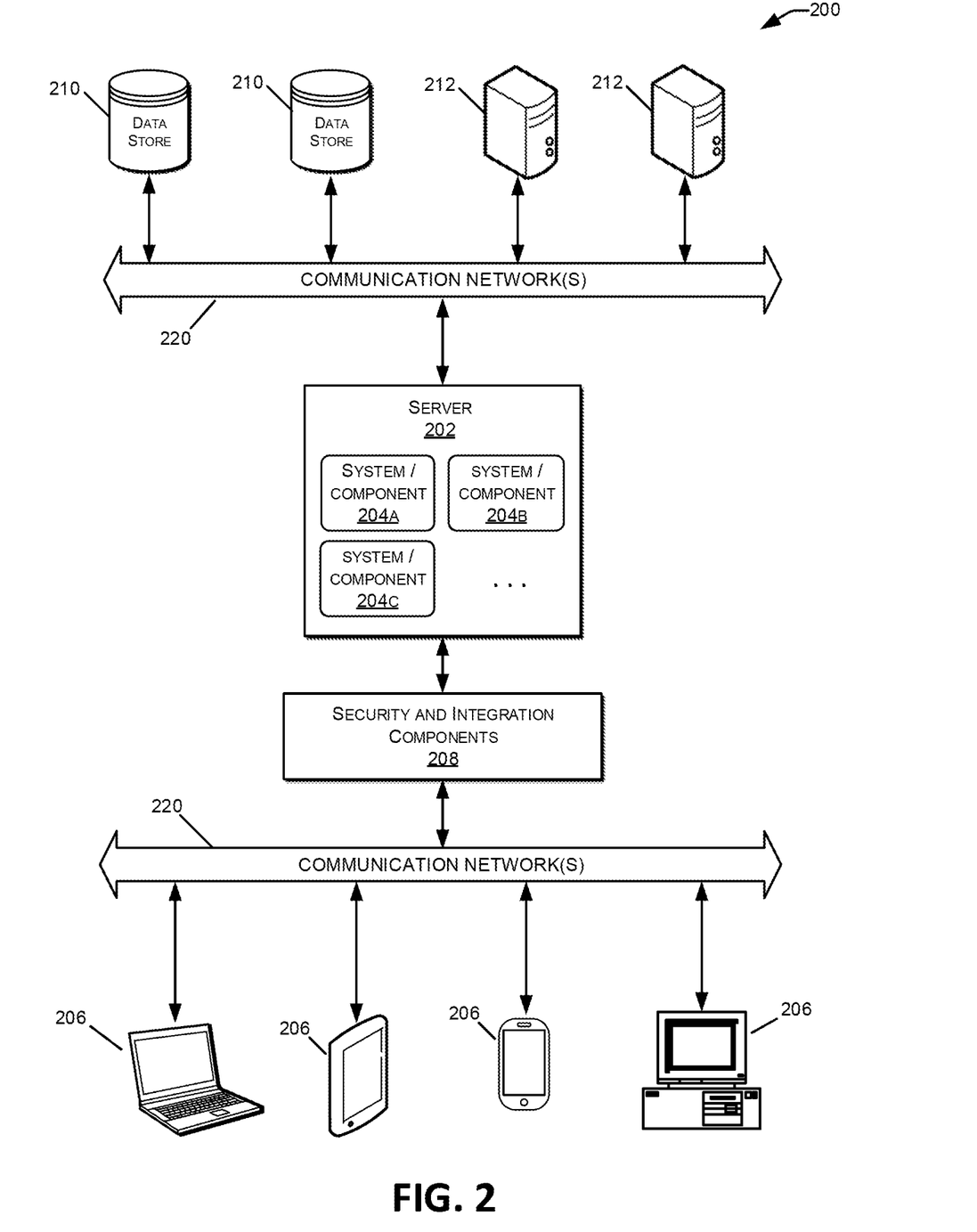
FIG. 2 is an illustrative distributed computing environment.

With reference to FIG. 2, an illustrative distributed computing environment 200 is shown including a computer server 202, four client computing devices 206, and other components that may implement certain embodiments and features described herein. In some embodiments, the server 202 may correspond to the server 106 and/or to the database server 108 discussed above in FIG. 1, and the client computing devices 206 may correspond to the devices used by, for example, the user 102. However, the computing environment 200 illustrated in FIG. 2 may correspond to any other combination of devices and servers configured to implement a client-server model or other distributed computing architecture.

Client devices 206 may be configured to receive and execute client applications over one or more networks 220. Such client applications may be web browser based applications and/or standalone software applications, such as mobile device applications. Server 202 may be communicatively coupled with the client devices 206 via one or more communication networks 220. Client devices 206 may receive client applications from server 202 or from other application providers (e.g., public or private application stores). Server 202 may be configured to run one or more server software applications or services, for example, web-based or cloud-based services, to support content distribution and interaction with client devices 206. Users operating client devices 206 may in turn utilize one or more client applications (e.g., virtual client applications) to interact with server 202 to utilize the services provided by these components.

Various different subsystems and/or components 204 may be implemented on server 202. Users operating the client devices 206 may initiate one or more client applications to use services provided by these subsystems and components. The subsystems and components within the server 202 and client devices 206 may be implemented in hardware, firmware, software, or combinations thereof. Various different system configurations are possible in different distributed computing systems 200 and networks 100. The embodiment shown in FIG. 2 is thus one example of a distributed computing system and is not intended to be limiting.

Although exemplary computing environment 200 is shown with four client computing devices 206, any number of client computing devices may be supported. Other devices, such as specialized sensor devices, etc., may interact with client devices 206 and/or server 202.

As shown in FIG. 2, various security and integration components 208 may be used to send and manage communications between the server 202 and user devices 206 over one or more communication networks 220. The security and integration components 208 may include separate servers, such as web servers and/or authentication servers, and/or specialized networking components, such as firewalls, routers, gateways, load balancers, and the like. In some cases, the security and integration components 208 may correspond to a set of dedicated hardware and/or software operating at the same physical location and under the control of the same entities as server 202. For example, components 208 may include one or more dedicated web servers and network hardware in a datacenter or a cloud infrastructure. In other examples, the security and integration components 208 may correspond to separate hardware and software components which may be operated at a separate physical location and/or by a separate entity.

Security and integration components 208 may implement various security features for data transmission and storage, such as authenticating users and restricting access to unknown or unauthorized users. In various implementations, security and integration components 208 may provide, for example, a file-based integration scheme or a service-based integration scheme for transmitting data between the various devices in the content distribution network 100. Security and integration components 208 also may use secure data transmission protocols and/or encryption for data transfers, for example, File Transfer Protocol (FTP), Secure File Transfer Protocol (SFTP), and/or Pretty Good Privacy (PGP) encryption.

In some embodiments, one or more web services may be implemented within the security and integration components 208 and/or elsewhere within the network 100. Such web services, including cross-domain and/or cross-platform web services, may be developed for enterprise use in accordance with various web service standards, such as RESTful web services (i.e., services based on the Representation State Transfer (REST) architectural style and constraints), and/or web services designed in accordance with the Web Service Interoperability (WS-I) guidelines. Some web services may use the Secure Sockets Layer (SSL) or Transport Layer Security (TLS) protocol to provide secure connections between the server 202 and user devices 206. SSL or TLS may use HTTP or HTTPS to provide authentication and confidentiality. In other examples, web services may be implemented using REST over HTTPS with the OAuth open standard for authentication, or using the WS-Security standard which provides for secure SOAP messages using XML, encryption. In other examples, the security and integration components 208 may include specialized hardware for providing secure web services. For example, security and integration components 208 may include secure network appliances having built-in features such as hardware-accelerated SSL and HTTPS, WS-Security, and firewalls. Such specialized hardware may be installed and configured in front of any web servers, so that any external devices may communicate directly with the specialized hardware.

Communication network(s) 220 may be any type of network familiar to those skilled in the art that can support data communications using any of a variety of commercially-available protocols, including without limitation, TCP/IP (transmission control protocol/Internet protocol), SNA (systems network architecture), IPX (Internet packet exchange), Secure Sockets Layer (SSL) or Transport Layer Security (TLS) protocols, Hyper Text Transfer Protocol (HTTP) and Secure Hyper Text Transfer Protocol (HTTPS), Bluetooth®, Near Field Communication (NFC), and the like. Merely by way of example, network(s) 220 may be local area networks (LAN), such as one based on Ethernet, Token-Ring and/or the like. Network(s) 220 also may be wide-area networks, such as the Internet. Networks 220 may include telecommunication networks such as public switched telephone networks (PSTNs), or virtual networks such as an intranet or an extranet. Infrared and wireless networks (e.g., using the Institute of Electrical and Electronics (IEEE) 802.11 protocol suite or other wireless protocols) also may be included in networks 220.

Computing environment 200 also may include one or more data stores 210 and/or back-end servers 212. In certain examples, the data stores 210 may correspond to the database server 108, and back-end servers 212 may correspond to all or portions of server 106. Data stores 210 and servers 212 may reside in the same datacenter or may operate at a remote location from server 202. In some cases, one or more data stores 210 may reside on a non-transitory storage medium within the server 202. Other data stores 210 and back-end servers 212 may be remote from server 202 and configured to communicate with server 202 via one or more networks 220. In certain embodiments, data stores 210 and back-end servers 212 may reside in a storage-area network (SAN), or may use storage-as-a-service (STaaS) architectural model.

Figure 3:
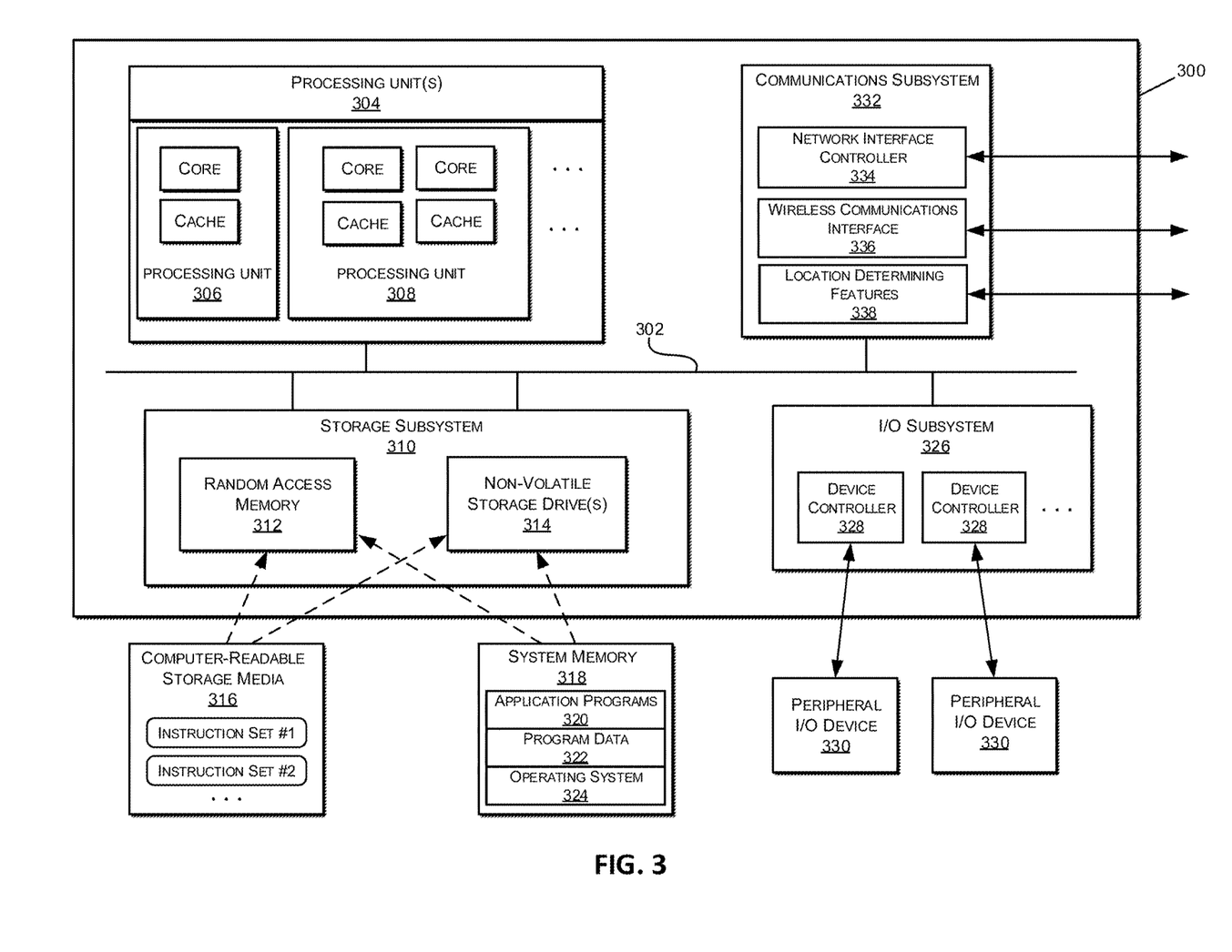
FIG. 3 is a block diagram of an illustrative computer system.

With reference now to FIG. 3, a block diagram of an illustrative computer system is shown. The system 300 may correspond to any of the computing devices or servers of the network 100 described above, or any other computing devices described herein, and specifically can include, for example, one or several of the user devices 203, and/or any of the servers 106, 108. In this example, computer system 300 includes processing units 304 that communicate with a number of peripheral subsystems via a bus subsystem 302. These peripheral subsystems include, for example, a storage subsystem 310, an I/O subsystem 326, and a communications subsystem 332.

Bus subsystem 302 provides a mechanism for letting the various components and subsystems of computer system 300 communicate with each other as intended. Although bus subsystem 302 is shown schematically as a single bus, alternative embodiments of the bus subsystem may utilize multiple buses. Bus subsystem 302 may be any of several types of bus structures including a memory bus or memory controller, a peripheral bus, and a local bus using any of a variety of bus architectures. Such architectures may include, for example, an Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, which can be implemented as a Mezzanine bus manufactured to the IEEE P1386.1 standard.

Processing unit 304, which may be implemented as one or more integrated circuits (e.g., a conventional microprocessor or microcontroller), controls the operation of computer system 300. One or more processors, including single core and/or multicore processors, may be included in processing unit 304. As shown in the figure, processing unit 304 may be implemented as one or more independent processing units 306 and/or 308 with single or multicore processors and processor caches included in each processing unit. In other embodiments, processing unit 304 may also be implemented as a quad-core processing unit or larger multicore designs (e.g., hexa-core processors, octo-core processors, ten-core processors, or greater.

Processing unit 304 may execute a variety of software processes embodied in program code, and may maintain multiple concurrently executing programs or processes. At any given time, some or all of the program code to be executed can be resident in processor(s) 304 and/or in storage subsystem 310. In some embodiments, computer system 300 may include one or more specialized processors, such as digital signal processors (DSPs), outboard processors, graphics processors, application-specific processors, and/or the like.

I/O subsystem 326 may include device controllers 328 for one or more user interface input devices and/or user interface output devices 330. User interface input and output devices 330 may be integral with the computer system 300 (e.g., integrated audio/video systems, and/or touchscreen displays), or may be separate peripheral devices which are attachable/detachable from the computer system 300. The I/O subsystem 326 may provide one or several outputs to a user by converting one or several electrical signals to user perceptible and/or interpretable form, and may receive one or several inputs from the user by generating one or several electrical signals based on one or several user-caused interactions with the I/O subsystem such as the depressing of a key or button, the moving of a mouse, the interaction with a touchscreen or trackpad, the interaction of a sound wave with a microphone, or the like.

Input devices 330 may include a keyboard, pointing devices such as a mouse or trackball, a touchpad or touch screen incorporated into a display, a scroll wheel, a click wheel, a dial, a button, a switch, a keypad, audio input devices with voice command recognition systems, microphones, and other types of input devices. Input devices 330 may also include three dimensional (3D) mice, joysticks or pointing sticks, gamepads and graphic tablets, and audio/visual devices such as speakers, digital cameras, digital camcorders, portable media players, webcams, image scanners, fingerprint scanners, barcode reader 3D scanners, 3D printers, laser rangefinders, and eye gaze tracking devices. Additional input devices 330 may include, for example, motion sensing and/or gesture recognition devices that enable users to control and interact with an input device through a natural user interface using gestures and spoken commands, eye gesture recognition devices that detect eye activity from users and transform the eye gestures as input into an input device, voice recognition sensing devices that enable users to interact with voice recognition systems through voice commands, medical imaging input devices, MIDI keyboards, digital musical instruments, and the like.

Output devices 330 may include one or more display subsystems, indicator lights, or non-visual displays such as audio output devices, etc. Display subsystems may include, for example, cathode ray tube (CRT) displays, flat-panel devices, such as those using a liquid crystal display (LCD) or plasma display, light-emitting diode (LED) displays, projection devices, touch screens, and the like. In general, use of the term "output device" is intended to include all possible types of devices and mechanisms for outputting information from computer system 300 to a user or other computer. For example, output devices 330 may include, without limitation, a variety of display devices that visually convey text, graphics, and audio/video information such as monitors, printers, speakers, headphones, automotive navigation systems, plotters, voice output devices, and modems.

Computer system 300 may comprise one or more storage subsystems 310, comprising hardware and software components used for storing data and program instructions, such as system memory 318 and computer-readable storage media 316. The system memory 318 and/or computer-readable storage media 316 may store program instructions that are loadable and executable on processing units 304, as well as data generated during the execution of these programs.

Depending on the configuration and type of computer system 300, system memory 318 may be stored in volatile memory (such as random access memory (RAM) 312) and/or in non-volatile storage drives 314 (such as read-only memory (ROM), flash memory, etc.). The RAM 312 may contain data and/or program modules that are immediately accessible to and/or presently being operated and executed by processing units 304. In some implementations, system memory 318 may include multiple different types of memory, such as static random access memory (SRAM) or dynamic random access memory (DRAM). In some implementations, a basic input/output system (BIOS), containing the basic routines that help to transfer information between elements within computer system 300, such as during startup, may typically be stored in the non-volatile storage drives 314. By way of example, and not limitation, system memory 318 may include application programs 320, such as client applications, Web browsers, mid-tier applications, server applications, etc., program data 322, and an operating system 324.

Storage subsystem 310 also may provide one or more tangible computer-readable storage media 316 for storing the basic programming and data constructs that provide the functionality of some embodiments. Software (programs, code modules, instructions) that when executed by a processor provide the functionality described herein may be stored in storage subsystem 310. These software modules or instructions may be executed by processing units 304. Storage subsystem 310 may also provide a repository for storing data used in accordance with the present invention.

Storage subsystem 310 may also include a computer-readable storage media reader that can further be connected to computer-readable storage media 316. Together and, optionally, in combination with system memory 318, computer-readable storage media 316 may comprehensively represent remote, local, fixed, and/or removable storage devices plus storage media for temporarily and/or more permanently containing, storing, transmitting, and retrieving computer-readable information.

Computer-readable storage media 316 containing program code, or portions of program code, may include any appropriate media known or used in the art, including storage media and communication media, such as, but not limited to, volatile and non-volatile, removable and non-removable media implemented in any method or technology for storage and/or transmission of information. This can include tangible computer-readable storage media such as RAM, ROM, electronically erasable programmable ROM (EEPROM), flash memory or other memory technology, CD-ROM, digital versatile disk (DVD), or other optical storage, magnetic cassettes, magnetic tape, magnetic disk storage or other magnetic storage devices, or other tangible computer readable media. This can also include nontangible computer-readable media, such as data signals, data transmissions, or any other medium which can be used to transmit the desired information and which can be accessed by computer system 300.

By way of example, computer-readable storage media 316 may include a hard disk drive that reads from or writes to non-removable, nonvolatile magnetic media, a magnetic disk drive that reads from or writes to a removable, nonvolatile magnetic disk, and an optical disk drive that reads from or writes to a removable, nonvolatile optical disk such as a CD ROM, DVD, and Blu-Ray® disk, or other optical media. Computer-readable storage media 316 may include, but is not limited to, Zip® drives, flash memory cards, universal serial bus (USB) flash drives, secure digital (SD) cards, DVD disks, digital video tape, and the like. Computer-readable storage media 316 may also include, solid-state drives (SSD) based on non-volatile memory such as flash-memory based SSDs, enterprise flash drives, solid state ROM, and the like, SSDs based on volatile memory such as solid state RAM, dynamic RAM, static RAM, DRAM-based SSDs, magnetoresistive RAM (MRAM) SSDs, and hybrid SSDs that use a combination of DRAM and flash memory based SSDs. The disk drives and their associated computer-readable media may provide non-volatile storage of computer-readable instructions, data structures, program modules, and other data for computer system 300.

Communications subsystem 332 may provide a communication interface from computer system 300 and external computing devices via one or more communication networks, including local area networks (LANs), wide area networks (WANs) (e.g., the Internet), and various wireless telecommunications networks. As illustrated in FIG. 3, the communications subsystem 332 may include, for example, one or more network interface controllers (NICs) 334, such as Ethernet cards, Asynchronous Transfer Mode NICs, Token Ring NICs, and the like, as well as one or more wireless communications interfaces 336, such as wireless network interface controllers (WNICs), wireless network adapters, and the like. As illustrated in FIG. 3, the communications subsystem 332 may include, for example, one or more location determining features 338 such as one or several navigation system features and/or receivers, and the like. Additionally and/or alternatively, the communications subsystem 332 may include one or more modems (telephone, satellite, cable, ISDN), synchronous or asynchronous digital subscriber line (DSL) units, FireWire® interfaces, USB® interfaces, and the like. Communications subsystem 336 also may include radio frequency (RF) transceiver components for accessing wireless voice and/or data networks (e.g., using cellular telephone technology, advanced data network technology, such as 3G, 4G or EDGE (enhanced data rates for global evolution), WiFi (IEEE 802.11 family standards, or other mobile communication technologies, or any combination thereof), global positioning system (GPS) receiver components, and/or other components.

The various physical components of the communications subsystem 332 may be detachable components coupled to the computer system 300 via a computer network, a FireWire® bus, or the like, and/or may be physically integrated onto a motherboard of the computer system 300. Communications subsystem 332 also may be implemented in whole or in part by software.

In some embodiments, communications subsystem 332 may also receive input communication in the form of structured and/or unstructured data feeds, event streams, event updates, and the like, on behalf of one or more users who may use or access computer system 300. For example, communications subsystem 332 may be configured to receive data feeds in real-time from users of social networks and/or other communication services, web feeds such as Rich Site Summary (RSS) feeds, and/or real-time updates from one or more third party information sources (e.g., external data source 313). Additionally, communications subsystem 332 may be configured to receive data in the form of continuous data streams, which may include event streams of real-time events and/or event updates (e.g., sensor data applications, financial tickers, network performance measuring tools, clickstream analysis tools, automobile traffic monitoring, etc.). Communications subsystem 332 may output such structured and/or unstructured data feeds, event streams, event updates, and the like to one or more data stores 108 that may be in communication with one or more streaming data source computers coupled to computer system 300.

Due to the ever-changing nature of computers and networks, the description of computer system 300 depicted in the figure is intended only as a specific example. Many other configurations having more or fewer components than the system depicted in the figure are possible. For example, customized hardware might also be used and/or particular elements might be implemented in hardware, firmware, software, or a combination. Further, connection to other computing devices, such as network input/output devices, may be employed. Based on the disclosure and teachings provided herein, a person of ordinary skill in the art will appreciate other ways and/or methods to implement the various embodiments.

Figure 4:
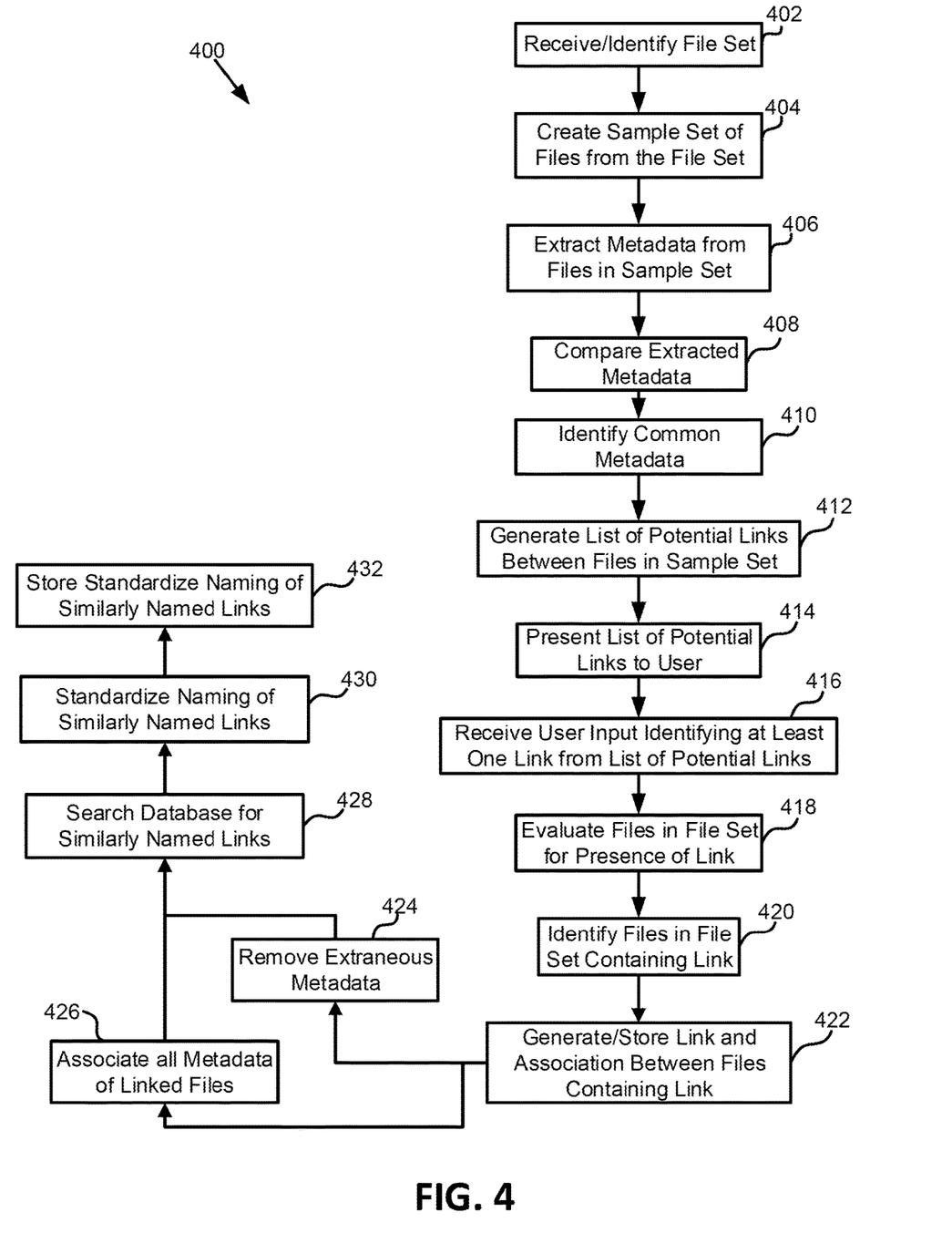
FIG. 4 is a flowchart illustrating one embodiment of a process for building a text-based search index.

With reference now to FIG. 4, a flowchart illustrating one embodiment of a process 400 for building a text-based search index is shown. In some embodiments, this process can include analyzing and inferring relationships within a flat file dataset that can contain, for example, images and image metadata. These analyzed and inferred relationship can then interlink the images and their metadata and can create a text-based search index. The process 400 can be performed, for example, by all or portions of network 100, and specifically by server 106 and/or database server 108. In some embodiments, this can include, for example, server 202 and/or one or several data stores 210, and/or one or several back-end servers 212.

In some embodiments, for example, large data sets can be received by, for example, the server. In one particular instance, such a large data set can include multiple files. Within this large data set of files can be multiple subsets of files, each of the subsets sharing some commonality. For example, in the instance of medical-related files, different subsets of files may exist, each of which subsets of files relates to a different patient. So, for example, a first subset of files may relate to a first patient, to a first study, or be generated by a first machine, and the second subset of files may relate to a second patient, a second study, or be generated by a second machine. Each of the first and second subsets of files can include one or several files which can include one or several different files such as, for example, image files, text files, test results, or the like.

In some embodiments, receipt of the large data set may not include receipt of information identifying the relationship between files in the large data set, or more specifically, may not include receipt of information identifying and/or delineating subsets of the files in the large data set. Thus, utility of the large data set is limited. The process 400 can take such a large data set and can analyze the large data set and inferring relationships between the files of the data set to identify and delineate different subsets of files with a large data set. These inferred relationships can be stored to thereby build a text-based search index.

The process 400 begins at block 402 wherein a file set is received and or identified. In some embodiments, the file set can be received by the server 106 and/or the database server 108. In some embodiments, some or all of the files in the set of files can have associated metadata. In some embodiments, the file set can be in the database server 108 and can be identified server 102.

At block 404 a sample set of files is created from the file set. In some embodiments, this can include the server 106 selecting a sample set of files. This sample set of files can be selected in any desired fashion, and can include any desired number of files. In some embodiments, the sample set of files can be randomly selected by, for example, the server 106. In some embodiments, the sample set of files can comprise a desired percent of the file set such as, for example, 1%, 2%, 3%, 5%, 10%, 15%, 20%, 25%, 30%, or any other or intermediate percent of the set of files. In some embodiments, the sample set of files can comprise a fixed size which can remain the same irrespective of the size of the set of files.

At block 406 metadata is extracted from files in the sample set of files. This metadata can be extracted by, for example, the server 106. In some embodiments, the extracting of the metadata can include the identification of metadata in the files of the sample set of files and/or identifying files in the sample set of files having metadata. In some embodiments, some or all of the files in the sample set of files can comprise a single file or can comprise an aggregation of a plurality of subfiles. In embodiments in which some or all of the files in the sample set of files comprise an aggregation of a plurality of subfiles, one of the subfiles can include the data of the file and others of the subfiles can include metadata of the file.

In some embodiments, extracting metadata from files in the sample set of files can include, for each file in the sample set of files, determining if the file includes associated metadata and/or determining if the file includes one or several subfiles containing metadata. In some embodiments, a subfile can be identified as containing metadata and/or potentially containing metadata based on the extension of that file. Specifically, for example, a subfile can be identified as containing or potentially containing metadata when the subfile has a .csv or .txt extension. This is particularly the case for subfiles of an image file, in other words, subfiles with a .csv or .txt extension that are associated with an image file can be identified as containing metadata or as potentially containing metadata.

At block 408 metadata extracted from the files in the sample set of files is compared. This comparison is a comparison of extracted data of different files within the sample set of files. This comparison can be performed by, for example, the server 106.

At block 410, common metadata between files in the sample set of files is identified. This common metadata can be identified based on the comparison of extracted data performed in block 408. In some embodiments, this common metadata can identify, for example, a common file format, common content of the files, a common source or author of the files, that the files relate to a common subject such as to a common patient, or the like. In some embodiments, the identification of common metadata can be performed by the server 106 by selecting one of the files, retrieving metadata of that file, and then comparing that retrieve metadata to metadata of one, some, or all of the other files in the sample set of files. In some embodiments in which metadata comprises one or several tags, this comparison can include comparison of the tags of the selected file to the tags of one, some, or all of the other files in the sample set of files. In embodiments in which some or all of these one or several tags comprise a key-value pair, this comparison can include a comparison of all or portions of the key-value pair to identify common metadata. This can include, for example, comparing metadata to identify commonality of keys of key-value pairs, and/or commonality of entire key-value pairs.

At block 412 a list of potential links between files in the sample set of files is generated. In some embodiments, a link can correspond to identified common metadata, and this list of potential links can identify links for some or all identified common metadata. In some embodiments, this list can comprise an ordered list that can be, for example, ordered according to the frequency with which a link, or more specifically the metadata represented by the link and/or associated with the link is identified in the files of the sample set of files. This list can be generated by the server 106 and can be presented to a user as indicated in block 414. In some embodiments, the presentation of the list of the user can include the server 106 sending the list to the user device 102 via, for example, the communication network 104.

A block 416 a user input is received identifying at least one of the links from the list of potential links. In some embodiments, this user input can be received by the server 106 from the user device 102. In response to receipt of this input, the server 106 can identify the at least one link associated with the input. In some embodiments, the server can identify the at least one link associated with the input as an actual link. This at least one links can include and/or be associated with common metadata between files in the sample set of files.

At block 418 files in the set of files are evaluated for presence of the at least one link identified in block 416. This evaluation can be performed by the server 106 and can include a comparison of metadata of some or all of the files in the set of files to each of the at least one links and/or to metadata included in and/or associated with each of the at least one links. In some embodiments, this evaluation can include selecting one of the files of the set of files, and determining if the selected file has associated metadata. When the selected file has associated metadata, that metadata can be compared to each of the at least one link identified in block 416, and specifically to metadata included in each of that at least one link and/or associated with each of that at least one link.

When metadata matching a link is identified within a file of the set of files, then that file is identified as containing the link. In some embodiments, and as a result of the evaluation of block 418, the server 106 can identify files in the file set containing the link as indicated in block 420. In some embodiments, each of the files identified in block 420 can contain one or more of the links identified in block 416, or in other words, each of the files identified in block 420 can have metadata matching and/or corresponding to metadata in at least one link and/or to metadata associated with at least one link.

At block 422 an association between files identified as containing a link is generated and/or stored. This can result in creation of subsets of files based the metadata of those files containing metadata of a common link and/or associated with a common link. In some embodiments, a file may be associated with one or several files which can belong to one or several subsets of files. Thus, if metadata of a files includes a first link and a second link, then that file may be associated with a first subset of files all having metadata containing that first link and a second subset of files all having metadata containing that second link. In some embodiments, the entirety of a files metadata may be contained in one or several links, and in some embodiments, a file may contain metadata not found in any link. In some embodiments, this generation and/or storing of the association between files identified as associated with metadata containing a common link can include the storing of these associations to thereby create an index of the different subsets of files. These associations can be generated by the server 106 and/or can be stored in the database server 108, and in some embodiments, can be stored in a database in the database server 108.

At block 424 extraneous metadata is removed from the files in the set of files. In some embodiments, extraneous metadata can be metadata not identified as matching any of the links identified in block 416. This extraneous metadata can be removed from the files in the set of files by the server 106 and/or by the database server 108. In some embodiments, for example, the server 106 can send request to the database server 108 identifying extraneous metadata and requesting the removal and/or deletion of this extraneous metadata.

In some embodiments, and alternative to block 424, at block 426 an association can be generated between extraneous metadata in files of a subset of files and the other files in that subset of files. This can, in some embodiments, impute metadata associated with one file to other files in the subset. In some embodiments, this imputed metadata can be used to generate further associations with other files in the set of files. In some embodiments, for example, steps 418 through 422 can be performed using imputed metadata of one or several files to identify one or several further associations of files. The association of block 426 can be performed by the server 106.

At block 428 the database of links and/or associations is searched to identify similar or similarly named links. For example, if a link identified metadata indicating a specific patient's name, similarly named links may include links having variations of that patient's name such as, for example the patient's first and last names, the patient's first, middle, and last names, the patient's first name, middle initial, and last name, or the like. In some embodiments, the identification of similarly named links can include the creation of one or several sets of links. Each of these set can include links having a similar name.

After similarly named links have been identified, and as indicated in block 430, the naming of similarly named links can be standardized. In some embodiments, this can include creating a name for this set of links. The standardizing of the naming of the similarly named links can be performed by the server 106. As indicated in block 432, the standardized naming of the similarly named links can be stored. In some embodiments, the standardized naming of the similarly named links can be stored by, for example, the database server 108.

Completion of process 400 creates an index of subsets of files with in the set of files. The subsets are based on the identification of metadata associated with files in the subsets and a common link. Upon creation of the index, a file request can be received. If the file request identifies a name of a subset of files, which name can be, for example, the standardized name or any of the similar names of that subset of files, then the index can return the files identified as belonging to that subset of files.

Figure 5:
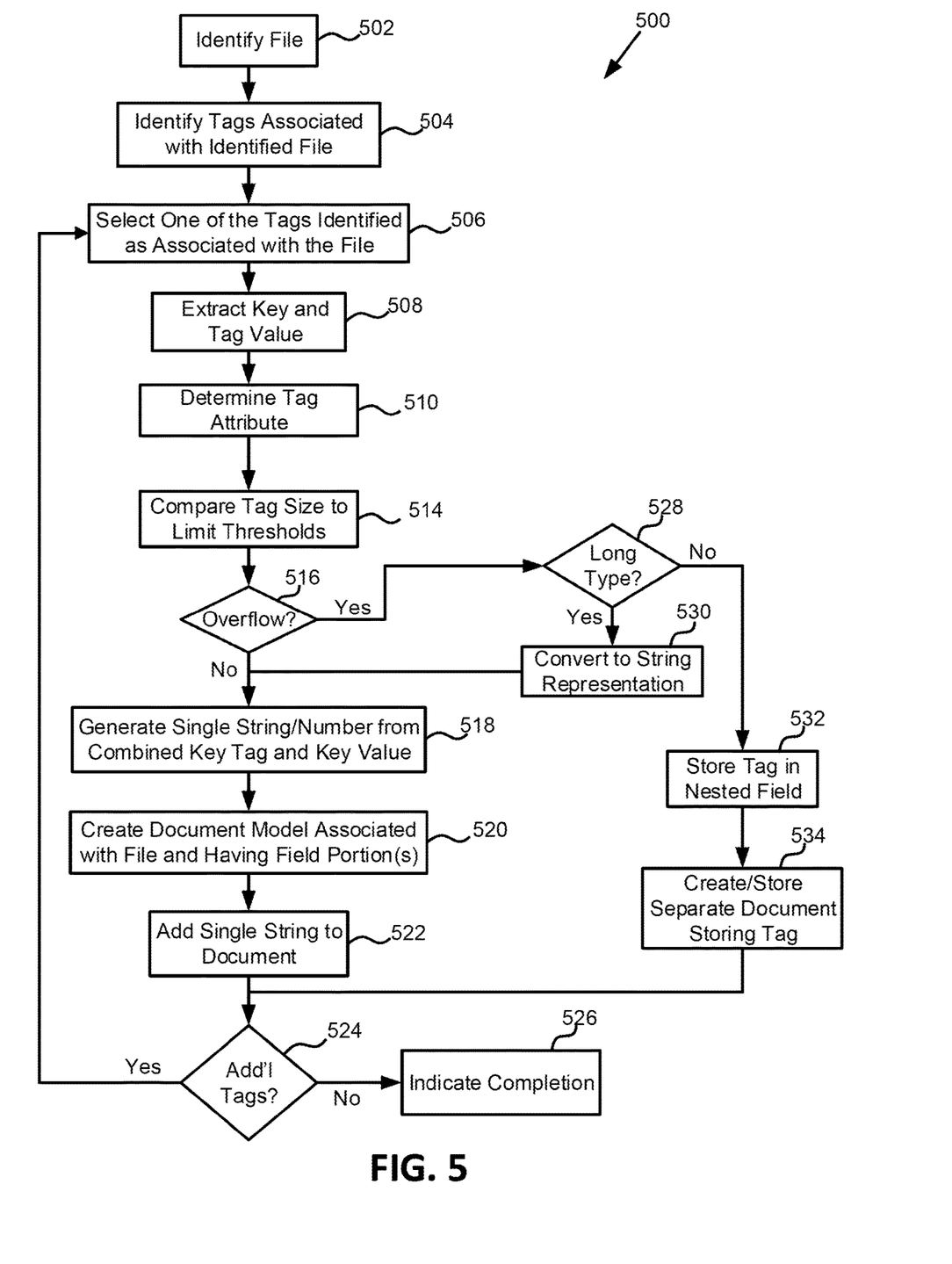
FIG. 5 is a flowchart illustrating one embodiment of a process for transforming and compressing tags of a file.

With reference now to FIG. 5, a flowchart illustrating one embodiment of a process 500 for transforming and compressing tags of a file is shown. The process 500 can be performed by the server 106. In some embodiments, by performing process 500 on files in a data set, total memory consumption by the data set can be decreased and searching of the data set can be improved, more specifically the speed with which the data set can be searched can be increased.

Before the process 500 begins, a plurality of files can be received and/or can be stored. These files can, in some embodiments, comprise DICOM files. These files can correspond to the set of files identified and/or received in block 402. In some embodiments, these files can be received by the server 106 and/or the database server 108. These files can be, for example, received from a user device 102.

The process 500 begins at block 502, wherein in a file is identified and/or selected. In some embodiments, this file can be one of the plurality of files and can be identified and/or selected by the server 106. At block 504 one or several tags associated with the identified file are identified. In some embodiments, each of these tags can comprise metadata of the identified file. In some embodiments, these tags can comprise DICOM tags. These tags can be identified by the server 106.

At block 506, one of the tags identified as associated with the file is selected. This tag can be selected by the server 106. This tag can comprise a key-value pair. In some embodiments, the key of the key-value pair can include a group and an element. In some embodiments, each of the group and the element comprise a two-byte number. In some embodiments, the key-value pair can include a tag value. In some embodiments, the tag value can comprise a string, which string can comprise a character string or a bit string representing a number. In some embodiments, the tag value can be represented by at least a two-byte integer number. At block 508 the key of the key-value pair, and the tag value of the key-value pair are extracted. In some embodiments, these can be extracted from the tag by the server 106.

At block 510, a tag attribute is determined. In some embodiments, this tag attribute can be determined by the server 106. In some embodiments, this tag attribute can characterize one or several aspects of the tag and/or information contained in the tag. In some embodiments, this tag attribute can identify the tag as comprising, for example, a string such as a character string, or a bit string representing a number. This tag attribute can further identify a number as, for example, a signed number, an unsigned number, or a floating point number. Thus, in some embodiments, determining the tag attribute can include determining that the tag, or in other words the key-value pair, is a string, determining that the tag, or in other words the key-value pair, is a number, determining that the tag, or in other words the key-value pair, is a signed number, determining that the tag, or in other words the key-value pair, is an unsigned number, or determining that the tag, or in other words the key-value pair, is a floating point number. In some embodiments, if it is determined that the tag, or in other words the key-value pair, is a number, determining the tag attribute further includes determining that the tag, or in other words the key-value pair, is one of: a signed number, an unsigned number, and a floating point number. In some embodiments, determining the tag attribute can further include determining a size of the tag. In some embodiments, determining the size of the tag can include determining the size of the number of the tag value.

At block 514 a size of the tag is compared to one or several limits thresholds which define a threshold range. In some embodiments, for example, a pair of limits thresholds can define upper and lower bounds of a threshold range. The size of the tag can be compared to the threshold range to determine if the size of the tag, or in other words, the number of the tag lies within the threshold range or outside of the threshold range.

In some embodiments, these limits may vary based on an attribute of the tag. For example, a first pair of limits may define a first threshold range for use when the number is a signed number, a second pair of limits may define a second threshold range for use when the number is an unsigned number, and/or a third pair of limits may define a third threshold range for use when the number is a floating point number. Thus, in some embodiments, comparing the tag to the threshold range and/or to the one or several limits thresholds can include selecting the threshold range and/or the one or several limits thresholds based on the attribute of the tag.

At decision step 516, it is determined if the tag size is within the threshold range, or in other words if the tag is an overflow tag. This determination can be made based on the comparison of block 514 by the server 106. In some embodiments, steps 514 and 516 are only performed if it is determined that the tag comprises a number including one of: a signed number; an unsigned number; and a floating point number. Thus, in embodiments in which the tag comprises a character string, the process 500 proceeds from step 510 to step 518.

If it is determined that the tag is a character string, or if it is determined that the tag size is within the threshold range, or in other words, the tag is not an overflow tag, then the process 500 proceeds to block 518 wherein a single string, which can be a single character string or bit string representing a number representing the entirety of the tag is generated. In some embodiments, the generation of the single string, which string can be character string or a bit string representing a number, can include the concatenation of the key and the tag value. In some embodiments, generating the single string representing the tag includes identifying the key of the tag and the tag value of the tag and combining the key and the tag value into a single string. In some embodiments, the single number can include a total of 64 bits, the first 32 bits of which represent the key of the key-value pair, and the second 32 bits of which represent the tag value of the key-value pair. More specifically, the first 16 bits of the single string represent the group, the next 16 bits to represent the element, and the remaining 32 bits to represent the tag value. Through this formatting of the single number, searches can be performed for an exact match, but also range queries can be applied to all or portions of the single string including to the key portions of the single string.

At block 520 a document model is created and associated with the file identified in block 502. In some embodiments, this document model, which can comprise a subfile to the file identified in block 500 to can have a field portion comprising a plurality of fields. In some embodiments, this plurality of fields can include a field for character strings, and a field for bit strings representing numbers. In some embodiments, the plurality of fields can include a field for character strings, a field for signed numbers, a field for unsigned numbers, a field for floating point numbers, a field for converted long type numbers and/or for hexadecimal numbers, and/or a nested field. In some embodiments, this document model can be created by the server 106.

At block 522, the single string generated in block 518 is added to the document model. In some embodiments, this includes selecting one of the plurality of fields of the field portion of the document model associated with the identified file a block 502, and adding the single string to that selected one of the plurality of fields. In some embodiments, the one of the plurality of fields can be selected according to the tag attribute of the tag for which the single string is generated, and the single string can be added to the field of the document model corresponding to the tag attribute of the tag selected in block 506 and for which the single string was generated. Thus, and by way of example, in embodiments in which the single string was generated for a tag comprising a character string, the single string is added to the field for character strings. Similarly, and by way of example, in embodiments in which the single number was generated for attack comprising a signed number, the single number is added to the field for signed numbers. Thus, in some embodiments, storing the single number in the selected one of the plurality of fields can include storing the single number in a first field when the tag represented by the single number comprises a signed number, storing the single number in a second field when the tag represented by the single number comprises an unsigned number, and storing the single number in a third field when the tag represented by the single string comprises a floating point number.

At decision step 524, it is determined if there are additional tags associated with the identified file and that have not been converted into single strings. If there are additional tags, than the process 500 returns to block 506 and proceeds as outlined above. If there are no additional tags, than the process 500 proceeds to block 526 and terminates and/or indicate completion of the process 500.

Returning again to decision step 516, if it is determined that the size of the tag is outside of the threshold range, then the process 500 proceeds to decision step 528 wherein it is determined if the tag is a long-type tag. In some embodiments, a tag can include information indicating whether it is a long-type tag, and determining if the tag is a long-type tag can include extracting this information from the tag. In some embodiments, this step can include determining if the tag is an unsigned, long-type tag. In such an embodiment signed, long-type tags can be stored natively within a nested field along with other signed overflow numbers. The determination of decision step 528 can be performed by the processor 106.

If it is determined that the tag is a long-type tag, than the process 500 proceeds to block 530 wherein the tag value is converted to a number representation of that tag value. In some embodiments such as for an unsigned long-type tag, this can include converting the number of the tag value into a hexadecimal number represented as a string, and specifically as a character string. After the tag value has been converted to a representative string, the process 500 proceeds to block 518 and continues as outlined above.

Returning again to decision state 528, if it is determined that the tag is not a long-type tag, then the process 500 proceeds to block 532 wherein the tag is stored in a nested field of the document model associated with the file of the tag. In some embodiments, storing the tag and the nested field can include creating and storing a separate document containing the tag as indicated in block 534. In some embodiments, storing the tag in the nested field can include putting a pointer to this separate document in the nested field. After the separate document containing the tag has been created and stored, the process 500 proceeds to decision step 524 and proceeds as outlined above.

A number of variations and modifications of the disclosed embodiments can also be used. Specific details are given in the above description to provide a thorough understanding of the embodiments. However, it is understood that the embodiments may be practiced without these specific details. For example, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments may be described as a process which is depicted as a flowchart, a flow diagram, a swim diagram, a data flow diagram, a structure diagram, or a block diagram. Although a depiction may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, and/or various other storage mediums capable of storing that contain or carry instruction (s) and/or data.

While the principles of the disclosure have been described above in connection with specific apparatuses and methods, it is to be clearly understood that this description is made only by way of example and not as limitation on the scope of the disclosure.

What is claimed is:

1. A system for automated file linking, the system comprising:
    at least one database server comprising stored data comprising a set of files, each of the files in the set of files comprising a digital file, at least some of the files comprising metadata; and
    at least one physical server configured to:
    create a sample set of files from the set of files;
    identify common metadata between files in the sample set of files;
    identify at least one link, wherein a link comprises the common metadata between files in the sample set of files;
    identify files in the set of files, each of the identified files containing the link in their metadata;
    generate an association between the files containing the link in their metadata;
    store the association between the files containing the link in their metadata;
    select at least one file from the set of files;
    identify a DICOM tag associated with each of the at least one files, the tag comprising a key-value pair;
    convert the DICOM tag into a single string;
    generate a document model associated with the selected file, the document model comprising a field portion comprising a plurality of fields, each of which plurality of fields is configured to contain a string;
    input the single string into one field of the plurality fields;
    receive a search request for searching in set of file; and
    search the document model based on the search request.

2. The system of claim 1, wherein the at least one database server is configured to receive the set of files.

3. The system of claim 2, wherein the at least one server is configured to create the sample set of files from the set of files.

4. The system of claim 1, wherein the at least one server is further configured to:
    extract metadata from files in the sample set of files; and
    compare metadata extracted from the files in the sample set of files, and wherein common metadata between files in the sample set of files is identified based on the comparing of metadata extracted from the files in the sample set of files.

5. The system of claim 4, wherein the at least one server is further configured to:
    generate a list of potential links, wherein the list of potential links identifies common metadata;
    present the list of potential links to a user; and
    receive a user input, wherein the at least one link is from the list of potential links and is identified based on the received user input.

6. The system of claim 1, wherein the at least one server is further configured to link all metadata of files containing the link in their metadata.

7. The system of claim 1, wherein the at least one server is further configured to delete extraneous metadata from associated files.

8. The system of claim 7, wherein extraneous metadata comprises metadata not in an identified link.

9. The system of claim 1, wherein the at least one server is further configured to:
    create a set of identified links; and
    standardize naming of the identified links.

10. The system of claim 9, wherein the at least one server is further configured to identify similar links among the identified links, and wherein standardizing naming of the identified links comprises consolidating similar links under a single link.

11. The system of claim 10, wherein the at least one server is further configured to store standardizingly named identified links.

12. A method of automated file linking comprising:
    creating a sample set of files from a set of files, each of the files in the set of files comprising a digital file, at least some of the files comprising metadata;
    identifying common metadata between files in the sample set of files from the file set;
    identifying at least one link, wherein a link comprises the common metadata between files in the sample set of files;
    identifying files in the set of files, each of the identified files containing the link in their metadata;
    generating an association between the files containing the link in their metadata;
    storing the association between the files containing the link in their metadata;
    selecting at least one file from the set of files;
    identifying a DICOM tag associated with each of the at least one files, the tag comprising a key-value pair;
    converting the DICOM tag into a single string;
    generating a document model associated with the selected file, the document model comprising a field portion comprising a plurality of fields, each of which plurality of fields is configured to contain a string;
    inputting the single string into one field of the plurality fields;
    receiving a search request for searching in set of file; and
    searching the document model based on the search request.

13. The method of claim 12, further comprising receiving a set of files.

14. The method of claim 13, further comprising creating a sample set of files from the set of files.

15. The method of claim 12, further comprising:
    extracting metadata from files in the sample set of files; and
    comparing metadata extracted from the files in the sample set of files, and wherein common metadata between files in the sample set of files is identified based on the comparing of metadata extracted from the files in the sample set of files.

16. The method of claim 15, further comprising:
    generating a list of potential links, wherein the list of potential links identifies common metadata;
    presenting the list of potential links to a user; and
    receiving a user input, wherein the at least one link is from the list of potential links and is identified based on the received user input.

17. The method of claim 12, further comprising linking all metadata of files containing the link in their metadata.

18. The method of claim 12, further comprising deleting extraneous metadata from associated files.

19. The method of claim 18, wherein extraneous metadata comprises metadata not in an identified link.

20. The method of claim 12, further comprising:
creating a set of identified links; and
standardizing naming of the identified links.

21. The method of claim 20, further comprising identifying similar links among the identified links, and wherein standardizing naming of the identified links comprises consolidating similar links under a single link.

22. The method of claim 21, further comprising storing standardizingly named identified links.

* * * * *